United States Patent
Brock-Fisher

(10) Patent No.: US 6,361,498 B1
(45) Date of Patent: Mar. 26, 2002

(54) CONTRAST AGENT IMAGING WITH SUPPRESSION OF NONLINEAR TISSUE RESPONSE

(76) Inventor: George A Brock-Fisher, 15 Webster St., Andover, MA (US) 01810

(*) Notice: Subject to any disclaimer, the term of this patent is extended or adjusted under 35 U.S.C. 154(b) by 0 days.

(21) Appl. No.: 09/502,512

(22) Filed: Feb. 11, 2000

(51) Int. Cl.$^7$ ................................. A61B 8/14
(52) U.S. Cl. ................................. 600/458
(58) Field of Search ................. 600/437, 443, 600/447, 444, 453–458; 73/625, 626; 367/7, 11, 130; 424/9.1, 9.32

(56) References Cited

U.S. PATENT DOCUMENTS

| | | | |
|---|---|---|---|
| 5,570,691 A | * 11/1996 | Wright et al. | 600/447 |
| 5,577,505 A | 11/1996 | Brock-Fisher et al. | |
| 5,632,277 A | 5/1997 | Chapman et al. | |
| 5,706,819 A | 1/1998 | Hwang et al. | |
| 5,785,656 A | * 7/1998 | Chiabrera et al. | 600/449 |
| 5,902,243 A | 5/1999 | Holley et al. | |
| 6,063,033 A | 5/2000 | Haider et al. | |

FOREIGN PATENT DOCUMENTS

EP  0913704 A2  5/1999

* cited by examiner

Primary Examiner—Marvin M. Lateef
Assistant Examiner—Ali M. Imam

(57) ABSTRACT

The method of the invention enhances echo responses from contrast agent in relation to echo responses from tissue, where the echo responses from tissue exhibit a relationship that conforms to a polynomial model while the echo responses from the contrast agent do not conform thereto. The method causes transmission of plural ultrasound signals into a body including the contrast agent, each of the plural ultrasound signals transmitted with a predetermined transmit gain factor. The echo signals resulting from the plural ultrasound signals are received and each thereof is received with a predetermined receive gain factor. The transmit gain factor and receive gain factor for each corresponding transmitted ultrasound signal and echo signal are set to render the polynomial model equal to zero. The received echo signals are then combined in a manner to eliminate a fundamental and at least one harmonic component that conform to the polynomial model so as to leave signal components that do not conform (i.e., those that result from the contrast agent).

13 Claims, 1 Drawing Sheet

CONTRAST AGENT IMAGING WITH SUPPRESSION OF NONLINEAR TISSUE RESPONSE

FIELD OF THE INVENTION

This invention relates to ultrasonic imaging of contrast agent and, more particularly, to an ultrasonic imaging method that enhances ultrasound returns from contrast agent by substantially reducing returns from tissue and blood.

BACKGROUND OF THE INVENTION

Currently, there are several techniques for imaging contrast agents in the body, which enhance the sensitivity to contrast agent relative to body tissue and clutter. These techniques exploit the non-linear behavior of contrast agents.

U.S. Pat. No. 5,577,505 to Brock-Fisher et al., assigned to the same Assignee as this Application, measures ultrasound response under multiple excitation levels. It is known that the ultrasound responses from contrast agent increase somewhat exponentially with increases in applied ultrasound pressure. In contrast responses from tissue and blood are substantially linear with increases in ultrasound energy. In the Brock-Fisher et al. patent, ultrasound responses are gain corrected by an amount that corresponds to the difference in excitation levels and are then subtracted. Because of this subtraction, most of the linear response that is characteristic of tissue is removed and what remains is the non-linear response that results from contrast agent.

U.S. Pat. No. 5,632,277 to Chapman et al. enhances the ultrasound returns from contrast agent by altering the carrier phase by 180 degrees as between two successive transmit events. The echo signals are measured and combined so that the linear components cancel, leaving the nonlinear components for analysis.

U.S. Pat. No. 5,706,819 to Hwang et al. inverts the polarity of the succeeding transmit waveforms. The echo signals received from the succeeding transmit events are combined and a harmonic response is obtained that enables the nonlinear echoes from contrast agent to be detected.

U.S. Pat. No. 5,902,243 to Holley et al. modulates the phase of one or more components of the transmit waveform. Received echoes are summed to selectively cancel the harmonic or fundamental components. Such action can either enhance the fundamental echo frequencies or the harmonic frequencies.

European Patent Application EP 0913704 A2 discloses an imaging method which separates broadband linear and nonlinear echo signal components. The method maps echo signals in the time domain to Doppler shift frequencies in the frequency domain in a manner that depends upon the linearity of the echoes. The method analyzes phase shifts between successive echoes and the resulting Doppler spectrum is separated into even and odd harmonics. The resulting signals are separated into phase shift information and linear and nonlinear components to enable discrimination of motion artifacts.

In all of the above listed techniques, there is no differentiation between the nonlinear effects that result from tissue echoes versus the nonlinear effects of that result from contrast agent echoes. At moderate to high transmit pressures, significant nonlinear signals arising from the body fluids and tissues are detected and reduce the ability to differentiate contrast agents from surrounding tissues.

Accordingly, notwithstanding the multiple methods mentioned above for enhancing echo returns from contrast agent, there still exists a need for an improved method for enhancement of contrast agent response that enables a differentiation between nonlinear returns from contrast agent and tissue.

SUMMARY OF THE INVENTION

The invention suppresses nonlinear echo signals arising from tissue, while allowing the nonlinear signals from the contrast agent to pass essentially unaffected for further processing. This is made possible due to a fundamental difference in the nonlinear response of body tissues, as compared with contrast agents. More particularly, the nonlinear response of tissues can be characterized as a "zero-memory" effect, in that the response of a scatterer in the tissue is proportional to the instantaneous acoustic pressure at the scatterer. However, the response of contrast agents has been found to be affected by the acoustic pressure waveform over a considerable period of time. Thus, contrast agents in acoustic pressure fields do not behave as zero memory systems. In other words, subsequent echo responses from contrast agent do not exhibit such a proportionality, as they are affected by previous contrast agent responses.

The method of the invention enhances echo responses from contrast agent in relation to echo responses from tissue, where the echo responses from tissue exhibit a relationship that conforms to a polynomial model while the echo responses from the contrast agent do not conform thereto. The method causes transmission of plural ultrasound signals into a body including the contrast agent, each of the plural ultrasound signals transmitted with a predetermined transmit gain factor. The echo signals resulting from the plural ultrasound signals are received and each thereof is received with a predetermined receive gain factor. The transmit gain factor and receive gain factor for each corresponding transmitted ultrasound signal and echo signal are set to render the polynomial model equal to zero. The received echo signals are then combined in a manner to eliminate a fundamental and at least one harmonic component that conform to the polynomial model so as to leave signal components that do not conform (i.e., those that result from the contrast agent).

DETAILED DESCRIPTION OF THE PREFERRED EMBODIMENT

Figure 1:
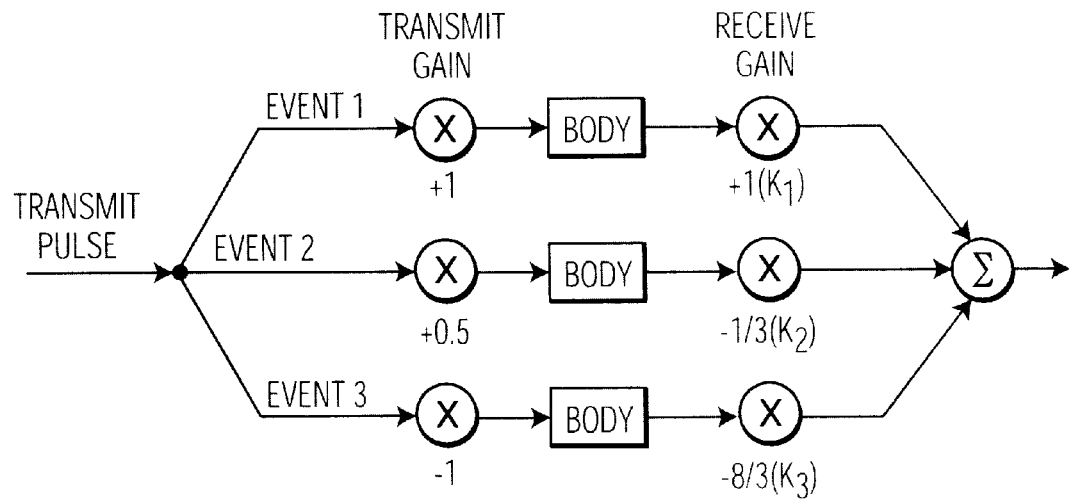
FIG. 1 schematically illustrates data manipulations of the invention on transmitted ultrasound signals and received echo signals.

Prior to describing a system embodiment that is adapted to carry out the invention, the method of the invention will be described. The response of body tissue to incident ultrasound pressure signals can be modeled as a "zero-memory" system, whose acoustic response "y" as a function of time "t" can be expressed as a function of the incident pressure "x", which is also a function of t. Thus, whenever the parameters y and x are set out below, it is to be understood that each is a function of (t). Further, the response of tissue (and blood) to an incident ultrasound signal is proportional to the incident signal and is not significantly affected by prior-in-time incident signals. The tissue response can be modeled as follows:

$$y = ax + bx^2 + cx^3 + \qquad \text{Eq.1}$$

where the $x$, $x^2$, $x^3$ . . . values are indicative of the fundamental, second harmonic and third harmonic responses. The parameters a, b and c are arbitrary constants The $cx^3$ term can be removed by imposition of a filter, as the third harmonic is characteristically a small value. Thus, equation 1 becomes:

$$y=ax+bx^2 \qquad \text{Eq. 2}$$

Thereafter, a plurality of transmit events are triggered (e.g., three transmitted pulses) to acquire a plurality of points along the polynomial curve represented by equation 2. In order to separate the points, gain factors of +1, +0.5 and −1 are used. It is to be understood that these gain values are merely for purpose of explanation, and other values are equally usable to achieve the desired curve values. Accordingly, over the three transmit events, equation 2 becomes:

$$y_1 = ax+bx^2 \text{ (transmit amplitude=+1x)} \qquad \text{Eq 3}$$

$$y_2 = 0.5ax+0.25bx^2 \text{ (transmit amplitude=+0.5x)} \qquad \text{Eq 4}$$

$$y_3 = -ax+bx^2 \text{ (transmit amplitude=-1x)} \qquad \text{Eq 5}$$

Each received echo signal ($y_n$) is then scaled by a gain factor ($k_n$) and the responses are summed. The object of this action is to find a value of k that causes $y_t$ to go to zero.

$$y_t = y1k_1 + y2k_2 + y3k_3 = k_1(ax+bx^2) + k_2(0.5ax+0.25bx^2) + k_3(-ax+bx^2) \qquad \text{Eq. 4}$$

The terms of equation 4 are now separated into the fundamental and second harmonic terms and each is set equal to 0, to result in the following:

$$0 = k_1(ax) + 0.5k_2(ax) - k_3(ax) \qquad \text{Eq. 5}$$

$$0 = k_1(bx^2) + 0.25k_2(bx^2) + k_3(bx^2) \qquad \text{Eq. 6}$$

Next, set $k_1 = 1$ and divide equation 5 by ax, and equation 6 by $bx^2$, to achieve the following:

$$0 = 1 + 0.5k_2 - k_3$$

$$k_2 = 2k_3 - 2 \qquad \text{Eq. 7}$$

and $$0 = 1 + 0.25k_2 + k_3 \qquad \text{Eq. 8}$$

Substituting equation 7 into equation 8 allows the value of $k_3$ to be derived as follows:

$$0 = 1 + 0.25(2k_3 - 2) + k_3$$

$$k_3 = -0.5/1.5 = -\tfrac{1}{3} \qquad \text{Eq. 9}$$

To solve for $k_2$, equations 7 and 9 lead to the following:

$$k_2 = 2(-\tfrac{1}{3}) - 2 = -\tfrac{8}{3} \qquad \text{Eq. 10}$$

Now it is known that the fundamental and second harmonic responses resulting from tissue response can be substantially eliminated by using transmit gain factors of +1, +0.5 and 1 and respective receive scaling factors of +1 (=$k_1$), −⅔ (=$k_2$) and −⅓ (=$k_3$) over three transmit events. Use of these factors and summation of the respective echo responses causes the fundamental and second harmonic responses to go to zero. The result is that only the response of contrast agent remains, which by virtue of having a memory effect, does not conform to the behavior of equation 1.

The action of the above data manipulations of the received echo signals is schematically illustrated in FIG. 1.

The succeeding transmit events may be combined as disclosed in U.S. Pat. No. 5,706,819, i.e., additive inversion. In the first transmit event, this inversion is inserted in the transmitted signal and the first response is:

$$y_1 = -ax+bx^2 - cx^3 + \ldots$$

For the second transmit event, (with inversion at the receiver, the second response is:

$$y_2 = -ax - bx^2 - cx^3 + \ldots$$

Subtracting the two responses gives:

$$y = 2bx^2 + 2dx^4 + \ldots$$

If the second transmit event is changed from inversion to unity-pass, the result of subtraction yields:

$$y = 2ax + 2cx^3 + \ldots$$

Again, the strong second harmonic response of tissues is cancelled. The linear and higher-order terms can be removed by filtering. As before, because the contrast agent does not behave as a zero-memory system, it is not suppressed by this processing technique.

It can be seen that this approach can be extended to techniques using more than three transmit lines. In this case, averaging the results of more than three transmit lines can improve signal-to-noise ratio. Additionally, phase effects can be examined to improve processing sensitivity. Furthermore, because the technique improves the sensitivity of an ultrasound system to contrast agent, it can be used advantageously to reduce either the amount of contrast agent introduced into the patient, or to reduce the acoustic pressure used to a level which is sufficiently low that the contrast agent is not destroyed by the imaging acoustic pulses. This allows the approach to be used in real-time imaging of contrast agents at relatively low acoustic pressures.

Figure 2:
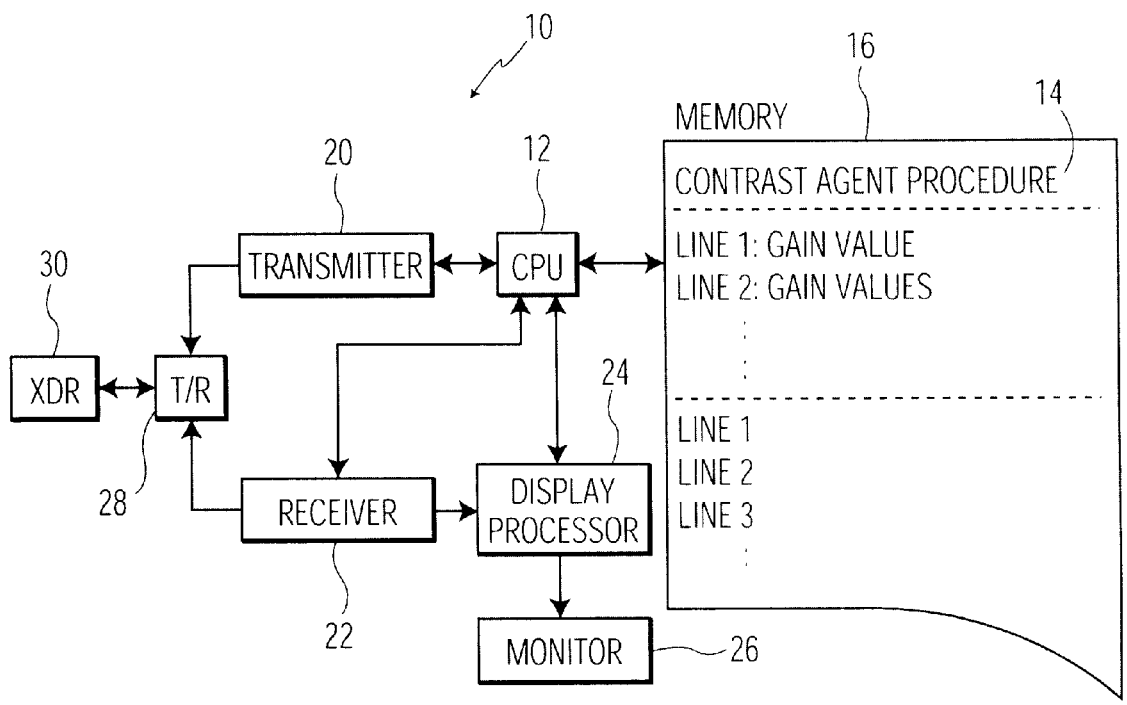
FIG. 2 is a high level block diagram of an ultrasound system that is adapted to carry out the method of the invention.

Turning now to FIG. 2, a high level block diagram of an ultrasound system 10 is shown that is adapted to carry out the method of the invention. System 10 includes a central processor 12 that is controlled by a contrast agent enhancement procedure 14 stored in memory 16. Procedure 14 includes instructions that cause the buffering of multiple lines of ultrasound echo responses and the adjustment of the respective transmit and receive gain factors that lead to such echo response lines. Further, procedure 14 also controls the summing of the respective echo signal values to result in an output of data values that represent the returns from the contrast agent (as described above).

Accordingly, to carry out the method of the invention, CPU 12 causes transmitter 20 to instruct transducer 30, via switch 28, to transmit succeeding ultrasound pulses with gain factors of, for example, +1, +0.5 and −1. The respective echo returns are received by receiver 22, via transducer 30, through switch 28. Receiver 22 applies receive gain factors of +1, −⅓ and −⅔, respectively. Thereafter, the received echo signals are converted to digital values, stored in memory 16 and summed to eliminate the first and second harmonic components that conform to the above-indicated equation 1. Higher frequency components may be eliminated by a filter function.

What is left are the signal components of the echo signals that do not conform to equation 1, i.e., the signals that exhibit a memory effect that results from interaction of the contrast agent with previously applied ultrasound signals. The processed signals are then dispatched to display processor 24 and are then displayed on monitor 26.

It should be understood that the foregoing description is only illustrative of the invention. Various alternatives and modifications can be devised by those skilled in the art without departing from the invention. For example, while the procedures required to implement the invention are shown in the drawings as already loaded into memory of the system. It is to be understood, however, that the procedures may be stored on removable memory media and loaded on an as needed basis. Accordingly, the present invention is intended to embrace all such alternatives, modifications and variances which fall within the scope of the appended claims.

What is claimed is:

1. An ultrasound method for enhancing echo responses from contrast agent in relation to echo responses from tissue, wherein said echo responses from tissue exhibit a relationship that conforms to a polynomial model while the echo responses from said contrast agent do not conform to said polynomial model, said method comprising the steps of:
   a) forming said polynomial model;
   b) transmitting plural ultrasound signals into a body including said contrast agent, each of said plural ultrasound signals transmitted with a transmit gain factor;
   c) receiving echo signals resulting from said plural ultrasound signals with a receive gain factor, said transmit gain factor and receive gain factor for each corresponding transmitted ultrasound signal and echo signal set to render said polynomial model equal to zero; and
   d) combining said received echo signals to eliminate a fundamental and at least one harmonic component that conform to said polynomial model so as to leave signal components that result from said contrast agent.

2. The method as recited in claim 1, wherein said polynomial model is represented by the expression:

$$y = ax + bx^2 + cx^3 + \ldots$$

where x, $x^2$, $x^3$ . . . are values indicative of fundamental, second harmonic and third harmonic responses and parameters a, b and c are arbitrary constants.

3. The method as recited in claim 1, wherein step b) causes transmission of at least three ultrasound signals with respective transmit gain factors of: +1, +0.5 and −1, and wherein step c) causes reception of said echo signals with respective receive gain factors of +1, −⅓ and −⅜.

4. The method as recited in claim 1, wherein step d) subtracts said received echo signals to eliminate the fundamental and the at least one harmonic component that conform to said polynomial model.

5. The method as recited in claim 1, wherein step d) subjects said received echo signals to a filter action to eliminate at least one of said fundamental or harmonic component.

6. The method as recited in claim 1, wherein step b) transmits said ultrasound pulses with opposed phase relationships.

7. A memory media including instructions for controlling an ultrasound system to enhance echo responses from contrast agent in relation to echo responses from tissue, wherein said echo responses from tissue exhibit a relationship that conforms to a polynomial model while the echo responses from said contrast agent do not conform to said polynomial model, said memory media comprising:

a) means for forming a polynomial model;
b) means for controlling the ultrasound system to transmit plural ultrasound signals into a body including said contrast agent, each of said plural ultrasound signals transmitted with a transmit gain factor;
c) means for controlling the ultrasound system to receive echo signals resulting from said plural ultrasound signals with a receive gain factor, said transmit gain factor and receive gain factor for each corresponding transmitted ultrasound signal and echo signal set to render said polynomial model equal to zero; and
d) means for controlling the ultrasound system to combine said received echo signals to eliminate a fundamental and at least one harmonic component that conform to said polynomial model so as to leave signal components that result from said contrast agent.

8. The memory media as recited in claim 7, wherein said polynomial model is represented by the expression:

$$y = ax + bx^2 + cx^3 + \ldots$$

where x, $x^2$, $x^3$ . . . are values indicative of fundamental, second harmonic and third harmonic responses and parameters a, b and c are arbitrary constants.

9. The memory media as recited in claim 7, wherein means b) controls the ultrasound system to transmit at least three ultrasound signals with respective transmit gain factors of: +1, +0.5 and −1, and wherein means c) controls the ultrasound system to receive said echo signals with respective receive gain factors of +1, −⅓ and −⅜.

10. The memory media as recited in claim 7, wherein means d) controls the ultrasound system to subtract said received echo signals to eliminate the fundamental and the at least one harmonic component that conform to said polynomial model.

11. The memory media as recited in claim 7, wherein means d) controls the ultrasound system to subject said received echo signals to a filter action to eliminate at least one of said fundamental or harmonic component.

12. The memory media as recited in claim 7, wherein means b) controls the ultrasound system to transmit said ultrasound pulses with opposed phase relationships.

13. An ultrasound method for enhancing echo responses from contrast agent, said method comprising the steps of:
   forming a polynomial model of tissue and the contrast agent;
   transmitting a plurality of ultrasound signals into a body including contrast agent;
   setting a transmit gain factor for each of said plurality of ultrasound signals transmitted into said body including contrast agent, and a receive gain factor for each corresponding received echo signal to render said polynomial model of tissue and the contrast agent equal to zero; and
   combining the received echo signals to eliminate a fundamental and at least one harmonic component that conforms to the polynomial model so as to leave signal components that result from said contrast agent.

* * * * *